US011000363B2

(12) United States Patent
Campin et al.

(10) Patent No.: US 11,000,363 B2
(45) Date of Patent: May 11, 2021

(54) ACCOMMODATING INTRAOCULAR LENS DEVICES, SYSTEMS, AND METHODS USING AN OPAQUE FRAME

(71) Applicant: Alcon Inc., Fribourg (CH)

(72) Inventors: John A. Campin, Southlake, TX (US); Costin E. Curatu, Crowley, TX (US); Luis Diaz-Santana, Royston (GB); Nicholas James Wooder, Royston (GB); Richard Lintern, Cambridgeshire (GB); Rita Stella, Royston (GB); Samuel Pollock, Hitchin (GB)

(73) Assignee: Alcon Inc., Fribourg (CH)

( * ) Notice: Subject to any disclaimer, the term of this patent is extended or adjusted under 35 U.S.C. 154(b) by 601 days.

(21) Appl. No.: 15/584,137

(22) Filed: May 2, 2017

(65) Prior Publication Data

US 2018/0318066 A1     Nov. 8, 2018

(51) Int. Cl.
*A61F 2/16* (2006.01)
*G02C 7/08* (2006.01)

(52) U.S. Cl.
CPC .......... *A61F 2/1627* (2013.01); *A61F 2/1624* (2013.01); *A61F 2/1648* (2013.01); *A61F 2/1621* (2013.01); *A61F 2002/169* (2015.04); *A61F 2002/1689* (2013.01); *A61F 2002/1696* (2015.04); *A61F 2250/0036* (2013.01); *G02C 7/083* (2013.01)

(58) Field of Classification Search
CPC .... A61F 2/1613; A61F 2/1624; A61F 2/1627; A61F 2/1629; A61F 2/1635; A61F 2/1637; A61F 2/1648; A61F 2002/1681; A61F 2002/1682; A61F 2002/1696

See application file for complete search history.

(56) References Cited

U.S. PATENT DOCUMENTS

| 4,932,966 A * | 6/1990 | Christie | A61F 2/1613 |
| | | | 623/6.13 |
| 8,834,566 B1 | 9/2014 | Jones | |
| 2004/0064182 A1 | 4/2004 | Kelman | |
| 2006/0206206 A1* | 9/2006 | Peyman | A61F 2/1651 |
| | | | 623/6.34 |
| 2008/0269891 A1 | 10/2008 | Hong et al. | |
| 2013/0245754 A1* | 9/2013 | Blum | A61F 2/1627 |
| | | | 623/6.13 |

(Continued)

FOREIGN PATENT DOCUMENTS

WO    2012/067994 A2    5/2012

OTHER PUBLICATIONS

Apple, D., "Influence of Intraocular Lens Material and Design on Postoperative Intracapsular Cellular Reactivity", Tr. Am. Ophth. Soc. (2000) 98:257-283.

(Continued)

*Primary Examiner* — William H Matthews

(57) ABSTRACT

Disclosed herein is an implantable accommodative IOL system for insertion into an eye of a patient, the system comprising: an optical element and a housing including an opaque frame. The optical element comprises an optical lens having variable optical power, and the opaque frame is circumferentially disposed around a periphery of the optical element.

20 Claims, 8 Drawing Sheets

(56) References Cited

U.S. PATENT DOCUMENTS

2014/0043672 A1  2/2014 Clarke et al.

OTHER PUBLICATIONS

Bae, S.H., et al, "In Vitro Biocompatibility of Various Polymer-Based Microelectrode Arrays for Retinal Prosthesis", IOVS, vol. 53:6 (May 2012) 2653-2657.
Bauer, T., "High Density Through Wafer via Technology", NSTI-Nanotech, vol. 3 (2007) 116-119; ISBN 1420061844.
Bowman, L. et al, "The Packaging of Implantable Integrated Sensors", IEEE Transactions on Biomed Eng, BME-33:2 (Feb. 1986) 248-255.
Brewer, P., "Traceable Measurements of Water Vapour Transmission Rate for High Performance Barrier Layers", Photonex 2012: Nanostructured Metal Oxide Thin Films, National Physical Lab. Presentation (Oct. 2012), 21 pgs.
Briand, D., et al, "Bonding properties of metals anodically bonded to glass", Sensors & Actuators A: Physical, 114:2-3 (2004) 543-549.
Candler, R. N. et al, "Long-Term and Accelerated Life Testing of a Novel Singl-Wafer Vacuum Encapsulation for MEMS resonators", J. of Microeletromech Sys., 15:6 (Dec. 2006) 1446; DOI: 10.1109/JMEMS.2006.883586.
Celina, M., et al, "Accelerated aging and lifetime prediction: Review of non-Arrhenius behaviour due to two competing processes", ELSEVIER, Polymer Degradation & Stability 90 (May 2005) 395-404.
Cheng, Y-T, et al, "A Hermetic Glass-Silicon Package Formed Using Localized Aluminum/Silicon-Glass Bonding", J. Microelectromechanical Sys. 10:3 (Sep. 2001) 392-399.
Chiao, M. et al, "Device-Level Hermetic Packaging of Microresonators by RTP Aluminum-to-Nitride Bonding", J. Microelectromech Syst. (Jun. 2006) 15:3, 515-522.
Cho, S. et al, "Optical Spectra of Indium-Tin-Oxide Films Deposited on Flexible Colorless Polyimide Substrates", J of Korean Phys Society 48:3 (Mar. 2006) 468-471.
Chow, E. Y., et al, "A Miniature-Implantable RF-Wireless Active Glaucoma Intraocular Pressure Monitor", IEEE Trans. on Biomed Circuits & Sys. 4:6 (Dec. 2010) 340-349.
Clausen, T., "Flexible Encapsulation Films & OLED Light Extraction Technology", Plastic Electron EU, Dresden, DE (Oct. 2009) 31 pgs.
Cowley, A., et al, "A Healthy Future: Plantinum in Medical Applications", Platinum Metals Rev., 55:2 (2011) 98-107.
De Segovia, J.L., "Physics of Outgassing", Institute de Fisica Aplicada, CETEF "L. Torres Quevedo", CSIC, Madrid, Spain (date unknown) 109-109.
Decharat, A. et al, "Novel Room-Temperature Wafer-To-Wafer Attachment and Sealing of Cavities Using Cold Metal Welding", IEEE Xplore, Micro Electro Mech Systems (Jan. 2007) 385-388; DOI: 10.1109/MEMSYS.2007.4433148, ISSN: 1084-6999.
Dodrill, D, "Developments in Clear High Barrier Packaging", Flexible Pkg Conf. (Mar. 2004) 1-31.
Donald, I. W. et al, "Recent developments in the preparation, characterization and applications of glass- and glass-ceramic-to-metal seals and coatings", J Mater Sci (2011) 46:1975-2000; DOI 10.1007/s10853-010-5095-y.
Exner, H. et al, "Laser welding of functional and constructional ceramics for Microelectronics", LHM Laserinstitut Hochschule Mittweida, Univ. of Applied Sci. (Jul. 1999) 7 pgs., Website: http://laz.hs-mittweida.de/3_forschung/50_keramik/9_veroeffentlichungen/default.asp?content=%2F3_forschung%2F50_keramik%2F9_veroeffentlichungen%2Flaser_welding.htm.
Foerster, M., "Design and realization of a simulator of prosthetic vision and inkjet printing platinum nanoparticles on a ceramic substrate", Univ. of New S Whales (Sep. 2008), 54 pgs.
Fonseca, M. A. et al, "Flexible Wireless Passive Pressure Sensors for Biomedical Applicatons [sic]", Solid-State Sensors, Actuators, & Microsys Workshop, Hilton Head Island, SC (Jun. 2006) 37-42.

Forehand, D. I. et al, "Wafer Level Micropackaging for RF MEMS Switches", ASME 2005 Pacific Rim Tech Conf. San Fran, CA (Jul. 2005) 2047-2051, DOI: 10.1115/ipack2005-73398.
Gaebler, F., "Laser glass cutting in flat panel display production", Coherent Inc. Application Report, Industrial Laser Solutions (Jun. 2008) 4 pgs.
Ganesan, K., et al, "An all-diamond, hermetic electrical feedthrough array for a retinal prosthesis", Biomaterials (2013) , 1-8.; http://dx.doi.org/10.1016/j.biomaterials.2013.10.040.
Garner, S. et al, "Flexible glass for device substrate and hermetic barrier applications", Corning Inc. (Sep. 2012) 19 pgs.
George, S. C. et al, "Transport phenomena through polymeric systems", Prog. Polym. Sci. 26 (2001) 985-1017.
Gietzelt, T. et al "Mechanical Micromachining by Drilling, Milling and Slotting", InTech (2012) 159-182, ISBN: 978-953-307-906-6.
Gilleo, K. et al, "Getters—Molecular Scavengers for Packaging", HDI (Jan. 2001) 26-29, www.hdi-online.com.
Gorscak, S., et al, "[Design Guidline #1] Designer's Guide for Laser Hermetic Sealing", Hybrid Circuit Technol (Aug. 1991), Lake Publishing, 11 pgs.
Green, T. et al, "Why Three Monolayers of Moisture Are Important", TJ Green Assoc., LLC, (date unknown), 1-7, http://www.tjgreenllc.com/node/109.
Guyer, Eric, et al, "Accelerated Testing of Active Implantable Medical Devices", NACE Internt'l Corrosion Conf. & Expo, Paper No. 09464 (2009) 1-18.
Haque, R.M. et al, "A 3D Implantable Microsystem for Intraocular Pressure Monitoring Using a Glass-In-Silicon Reflow Process", MEMS, Cancun, MX, (Jan. 2011) 995-998; DOI: 10.1109/MEMSYS.2011.5734595.
Haque, R.M., et al, "An Intraocular Pressure Sensor Based on a Glass Reflow Process", Solid-State Sensors, Actuators, & Microsys Workshop, Hilton Head Island, SC (Jun. 2010) 49-52; http://web.eecs.umich.edu/~rhaque/papers/An%20Intraocular%20Pressure%20Sensor%20Based%20on%20a%20Glass%20Reflow%20Process.pdf.
Harpster, T. J. et al, "Long-Term Testing of Hermetic Anodically Bonded Glass-Silicon Packages", IEEE Xplore Micro Electro Mech Sys (Aug. 2002) 423-426; DOI:10.1109/MEMSYS.2002.984293, ISSN: 1084-6999.
Hench, L. L., "Bioceramics: From Concept to Clinic", J Am Ceram Soc. 74:7 (1991) 1487-510.
Hetke, J. F. et al, "Flexible Miniature Ribbon Cables for Long-term Connection to Implantable Sensors", ELSEVIER Sensors andActuators, A21-A23 (1990) 999-1002.
Hofmann, U., et al, "High-Q MEMS Resonators for Laser Beam Scanning Displays", Michromachines, vol. 3 (2012) 509-528; ISSN 2072-666X.
Hornig, R. et al, "The IMI Retinal Implant System", Artificial Sight, Basic Research, Biomed Eng & Clinical Adv (2007) 111-128; DOI 10.1007/978-0-387-49331-2_6; ISSN 1618-7210.
Hukins, D. W. L., et al, "Accelerated aging for testing polymeric biomaterials and medical devices", ELSEVIER, Med Eng & Physics (Jun. 2008) 1270-1274.
Iida, T. et al, "Preparation for Hydrogen Permeation Measurement through Ceramic Disc Samples", NIFS Repository, website: https://nifs-repository.repo.nii.ac.jp/index.php?, 1 pg.
Ino, T., et al, "Development of 3He polarized neutron spin filters at KEK", Physica B: Condensed Matter, 356:1-4 (Feb. 2005) 7 pgs.
Jiang, G., et al, "Technology Advances and Challenges in Hermetic Packaging for Implantable Medical Devices", Implantable Neural Prostheses 2, Springer, NY (2009) 27-61.
Jousten, K., "Thermal Outgassing", Physikalisch-Technische Bundesanstalt, Berlin, Germany (1999), 111-125.
Karbasi, A., et al, "Cofired Platinum/Alumina Microsystems for Implantable Medical Applications", J. Microelectronics. 42:4 (2012) 245-253.
Kim, J. S. et al, "Fluxless silicon-to-alumina bonding using electroplated Au—Sn—Au structure at eutectic composition", ELSEVIER Mat Sci & Eng A, 458 (2007) 101-107.
Knechtel, R., "Glass Frit Wafer Bonding", Handbook of Wafer Bonding, 1st Ed., (2012) 16 pgs.

(56) References Cited

OTHER PUBLICATIONS

Knudsen, A., et al, "Ceramic Packaging in Medical Applications", KYOCERA America, Inc., IMAPS Med Technol ATW, 1-48; https://americas.kyocera.com/assets/001/5258.pdf.

Kostinski, S. et al, "Diffusion of Water Molecules in Amorphous Silica", IEEE Electron Device LTRS 33:6 (Jun. 2012) 863-865.

Kotzar, G. et al, "Evaluation of MEMS materials of construction for implantable medical devices", ELSEVIER Biomaterials 23 (2002) 2737-2750.

Lee, S. W. et al, "Development of Microelectrode Arrays for Artificial Retinal Implants Using Liquid Crystal Polymers", Invest Ophthalmol & Vis Sci. 50:12 (Dec. 2009) 5859-5866.

Li, W. et al, "Wafer-Level Parylene Packaging With Integrated RF Electronics for Wireless Retinal Prostheses", J Microelectromech Sys. 19:4 (Aug. 2010) 735-742.

Lin, L, "MEMS Post-Packaging by Localized Heating and Bonding", IEEE Transactions on Advanced Packaging (Nov. 2000) 23:4, 608-616.

Liu, C. R. et al, "Field-assisted diffusion bonding and bond characterization of glass to aluminum", J Mater Sci. vol. 43 (2008) 5076-5082; DOI 10.1007/s10853-008-2583-4.

Lloyd, A. W. et al, "Ocular biomaterials and implants", ELSEVIER Biomaterials 22 (2001) 769-785.

Lombardo, M., et al, "Analysis of intraocular lens surface adhesiveness by atomic force microscopy", J Cataract Refract Surg. vol. 35 (Jul. 2009) 1266-1272.

Margomenos, A. et al, "Fabrication and Accelerated Hermeticity Testing of an On-Wafer Package for RF MEMS", IEEE Transactions on Microwave Theory and Techniques 52:6 (Jun. 2004) 1626-1636; DOI 10.1109/TMTT.2004.828467.

Marinis, T. F. et al, "Vacuum Sealed MEMS Package with an Optical Window", IEEE Xplore, Electr Components & Tech Conf (May 2008) 804-810; DOI: 10.1109/ectc.2008.4550067.

Marquardt, K. et al, "Development of near hermetic silicon/glass cavities for packaging of integrated lithium micro batteries", Microsyst Technol, vol. 16 (2010) 1119-1129.

Mayr, W., et al, "Basic design and construction of the Vienna FES implants: existing solutions and prospects for new generations of implants", ELSEVIER, Medical Eng & Physics 23 (Feb. 2001) 53-60.

McLoone, E. et al, "Silicone oil-intraocular lens interaction: which lens to use?", Br J Ophthalmol (2001) 85:543-545 DOI: 10.1136/bjo.85.5.5430.

Mensah, A. et al, "The Role of Permeability and Ion Transport in Conformal Coating Protection", National Physical Lab. NPL Report DEPC MPR 032 (Sep. 2005) 37 pgs.

Meyer, J-U, et al, "High Density Interconnects and Flexible Hybrid Assemblies for Active Biomedical Implants", IEEE Transactions on Adv. Packaging, 24:3 (Aug. 2001) 366-371.

Mihov, D. et al, "Some Biocompatible Materials Used in Medical Practice", Trakia J of Sciences, 8:2 (2010) 119-125; ISSN 1313-3551.

Fischer, J., presented by, MOCON Webinar Series, "Different Test Methods for High Barrier WVTR Testing" (Jun. 2010) 28 pgs.

Moshey, E.A., "A Compilation of Outgassing Data on Vacuum Materials", Princeton Univ. Plasma Physics Lab James Forrestal Campus (Feb. 1982) ETM82-001, 22 pgs.

Myllymaa, S., et al, "Flexible implantable thin film neural electrodes", INTECH Recent Advances in Biomed. Engineering (2009), 28 pgs; ISBN: 978-953-307-004-9.

Najafi, K. et al, "Micropackaging Technologies for Integrated Microsystems: Applications to MEMS and MOEMS" Proc. of SPIE (Jan. 2003) vol. 4979, 1-19; DOI: 10.1117/12.484953.

Najafi, K., "Packaging of Implantable Microsystems", IEEE Xplore Sensors 2007 (Dec. 2007) 58-63; DOI: 10.1109/ICSENS.2007.4388335, ISSN: 1930-0395.

Newman, J. et al, "Optical Leak Testing of Hermetic Semiconductor, MEMS and Optoelectronic Devices", SPIE ETATS-UNIS vol. 4931 (Sep. 2002) 641-649, ISBN 0-930815-66-1.

Nisato, G. et al, "Permeation Methods", Public Report, Info. Soc. Tech. (Sep. 2002) IST-2001-34215 FLEXled-phr-0209-009/Nisato, 23 pgs.

Nollau, S., "High Precision Optics Production with Precision Glass Moulding" Publishable Summ. Production4μ Project; Fraunhofer Inst. for Production Tech., 10 pgs.

Nörenberg, H., "Permeation Measurements at 0.001 g/m2/day and below for Applications in Flexible Electronics", www.technolox.com/pdf/profilex2007.pdf, 4 pgs.

Park, J-S et al, "Line Bonding of Wafers Using Transmission Laser Bonding Technique for Microsystem Packaging", IEEE Xplore (Jul. 2006) DOI: 10.1109/ITHERM.2006.1645503, ISSN: 1087-9870, 7 pgs.

Plobi, A. et al, "Wafer direct bonding: tailoring adhesion between brittle materials", Reports: A Review Journal, Mat. Sci & Eng, R25 (1999) 1-88.

Ramesham, R, "Evaluation of Non-Evaporable Getters for High Vacuum Hermetic Packages", Jet Propulsion Lab, CALTECH, JPL D-27440, 31 pgs.

Receveur, R. A. M. et al, "Microsystem technologies for implantable applications", J. Micromech. Microeng. 17 (Apr. 2007) R50-R80, DOI: 10.1088/0960-1317/17/5/R02.

Rizzo, J.F., "The Retinal Implant Project", Boston MA (2011) 29-1 thru 29-10.

Rodger, D. C., et al, "Flexible Circuit Technologies for Biomedical Applications", INTECH Advances in Micro/Nano Eletromech. Syst. & Fab. Technol. (2013) 39 pgs; DOI:10.5772/55308.

Scheidegger, S. et al, "Silica fibres with a metallic core", Inst. Appl. Phys. [Publications] Univ. of Bern, 9 pgs.

Schneider, A. et al, "Flexible Interconnects for Biomedical Microsystems Assembly" IMAPS Conf, Fraunhofer Inst Biomed Eng IBMT, Sulzbach DE (Jan. 2001) 18 pgs.

Schneider, a. et al, "Implantable Flexible Electrodes for Functional Electrical Stimulation", Medical Device Technology (Jan./Feb. 2004) 3 pgs; www.medicaldevicesonline.com.

Schuettler, M. et al, "Fabrication and Test of a Hermetic Miniature Implant Package with 360 Electrical Feedthroughs", IEEE EMBS, 32nd Ann Int'l Conf. (2010) Buenos Aires, AR 1585-1588.

Sedore, B.W.C., "Laser Welding of Alumina Ceramic Substrates with Two Fixed Beams", Mech & Materials Eng. Thesis, Queen's Univ. Grad. Prog.(Apr. 2013), 145 pgs.

Seigneur, F. et al, "Laser Soldered Packaging Hermeticity Measurement Using Metallic Conductor Resistance", Electron Tech Internet J., (Nov. 2006) 37/38 (2005/2006), 8, 4 pgs.

Singh, A., et al, "Improving Mechanical Stiffness of Coated Benzocyclobutene (BCB) Based Neural Implant", IEEE EMBS 26th Ann. Int'l Conf., San Francisco, CA (Sep. 2004) 4298-4301.

Sparks, D., et al, "Long-term evaluation of hermetically glass frit sealed silicon to Pyrex wafers with feedthroughs", J. Micromech. Microeng.15 (2005) 1560-1564, DOI: 10.1088/0960-1317/15/8/026.

Stieglitz, T., et al, "A Flexible Retina Implant for People Suffering From Retinitis Pigmentosa", Conference Proceedings, 4th Ann. Conf. Internt'l EFSS, Sendai, Japan (Aug. 1999) 4 pgs., http://ifess.org/proceedings/IFESS1999/IFESS1999_007_Stieglitz.pdf.

Stieglitz, T., et al, "Manufacturing, assembling and packaging of miniaturized neural implants", Microsyst Technol (2010) 16, 723-734; DOI 10.1007/s00542-009-988-x.

Sugiyama, K., et al, "A simplified method for manufacturing glass-insultated metal microelectrodes", J of Neuroscience Methods, 53 (1994) 73-80.

Green, "TM 1014 Update and Mermeticity Spec Change", MIL-STD-883J Microcircuits Revision J/Change 5 (2013) 3 pgs.

Tomsia, A. P., et al, "Joining Alumina to Sapphire for Copper Vapor Laser Tubes", Final Report to Naval Coastal Sys. Cntr under DITC Contr. N61331-90-C-0005 (Sep. 1990) 75 pgs.

VanHoestenberghe, A. et al., "Hermetic Encapsulation of an Implantable Vision Prosthesis—Combining Implant Fabrication Philosophies", Conference Paper, IFESS (2008) 3 pgs.

VanHoestenberghe, A., et al, "Corrosion of silicon integrated circuits and lifetime predictions in implantable electronic devices", J. Neural Eng. 10 (2013) 031002, 1-13.

(56) References Cited

OTHER PUBLICATIONS

Visser, R. J., "Barix Multilayers: a Water and Oxygen Barrier for Flexible Organic Electronics", VITEX Systems, MIT-Stanford-UC Berkeley Nano Forum, 28 pgs.
Weiland, J. D. et al, "Visual Prosthesis", IEEE Xplore, Proceedings, 96:7 (Jul. 2008) 1-9; DOI: 10.1109/JPROC.2008.922589.
Werner, L., "Biocompatibility of intraocular lens materials", Curr Opin Ophthalmol, vol. 19 (2008) 41-49.
Wu, Q. et al, "Glass Frit as a Hermetic Joining Layer in Laser Based Joining of Miniature Devices", IEEE Transactions on Components and Packaging Tech, 33:2 (Jun. 2010) 470-477.

\* cited by examiner

ACCOMMODATING INTRAOCULAR LENS DEVICES, SYSTEMS, AND METHODS USING AN OPAQUE FRAME

TECHNICAL FIELD

This disclosure relates generally to the field of ophthalmic lenses and, more particularly, to electro-active ophthalmic lenses.

BACKGROUND

The human eye provides vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light that can be transmitted to the retina. This deficiency in the lens of the eye is medically known as a cataract. Presently, cataracts are treated by surgical removal of the affected lens and replacement with an artificial intraocular lens ("IOL"). Cataract extractions are among the most commonly performed operations in the world.

In the natural lens, distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. Furthermore, the ciliary muscle loses flexibility and range of motion. This makes it harder for the lens to focus on near objects, a medical condition known as presbyopia. Presbyopia affects nearly all adults upon reaching the age of 45 to 50.

One approach to providing presbyopia correction is the use of an ophthalmic lens, such as an IOL. Single focal length or monocular IOLs have a single focal length or single power; thus, single focal length IOLs cannot accommodate, resulting in objects at a certain point from the eye being in focus, while objects nearer or further away remain out of focus. Single focal length IOLs generally do not require power to function properly. An improvement over the single focal length IOL is an accommodating IOL, which can actually change focus by movement (physically deforming and/or translating within the orbit of the eye) as the muscular ciliary body reacts to an accommodative stimulus from the brain, similar to the way the natural crystalline lens focuses. Such accommodating IOLs are generally made from a deformable material that can be compressed or distorted to adjust the optical power of the IOL over a certain range using the natural movements of eye's natural zonules and the ciliary body. In some instances, the accommodative IOL includes an electro-active element that has an adjustable optical power based on electrical signals controlling the element, so that the power of the lens can be adjusted based on the patient's physiologic accommodation demand.

The various components of an electro-active or electrically actuated IOL, however, often create an undesirably large implant that is difficult to implant in the eye through a small incision. A large incision can result in surgical complications such as vision loss secondary to scarring or trauma to ocular tissues. Moreover, an electro-active IOL requires power to function correctly, rendering patients vulnerable to poor visual quality in the case of a non-operational IOL experiencing a power or system failure.

The devices, systems, and methods disclosed herein overcome one or more of the deficiencies of the prior art.

SUMMARY

In one exemplary aspect, the present disclosure is directed to an implantable accommodative IOL system for insertion into an eye of a patient, the system comprising: an optical element and an opaque frame. In one aspect, the optical element comprises an optical lens having variable optical power, and a housing comprising an opaque frame circumferentially disposed around a periphery of the optical element.

In one aspect, the housing comprises a transparent anterior window and a transparent posterior window, the opaque frame circumferentially encircles the transparent anterior window and the transparent posterior window, and the optical element is positioned between the transparent anterior window and the transparent posterior window.

In one aspect, the optical element comprises an electrically responsive active element having a first thickness and first refractive index.

In one aspect, the optical element comprises tunable optics technology.

In one aspect, the opaque frame is shaped and configured to mimic the peripheral outline of the optical element.

In one aspect, the device includes at least one peripheral housing shaped and configured to contain electrical components and connections to the optical element.

In one aspect, the device includes at least one support leg shaped and configured to house electrical connections extending between the electrical components in the housing and the optical element. In one aspect, the at least one support leg comprises a hollow, tubular structure extending between the housing and the opaque frame. In one aspect, the at least one support leg is shaped as a linear support extending between the opaque frame and the housing. In one aspect, the at least one support leg is shaped as a curved support extending between the opaque frame and the housing. In one aspect, the at least one support leg is optically clear.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 6A illustrates a front view of the exemplary accommodative IOL device, and FIG. 6B illustrates a perspective view of the exemplary accommodative IOL device.

DETAILED DESCRIPTION

Figure 1:
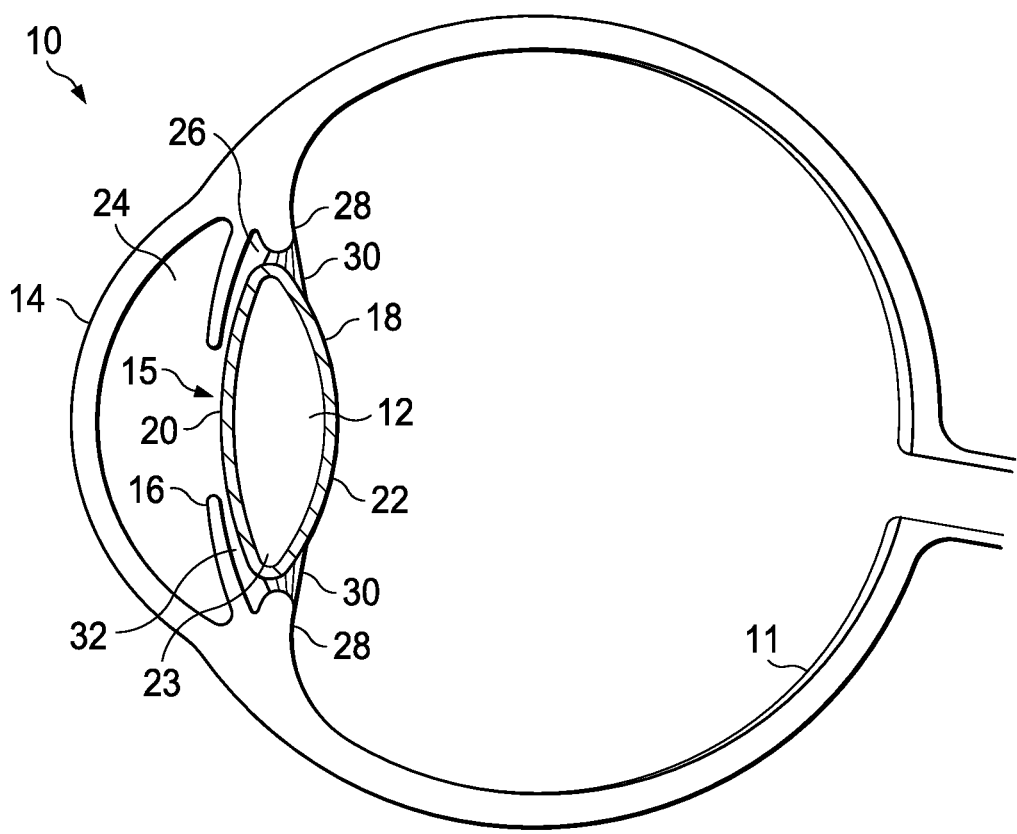
FIG. 1 is a diagram of a cross-sectional side view of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for use in alleviating ophthalmic conditions, including visual impairment secondary to presbyopia, cataracts, and/or macular degeneration. As described above, electrically actuated accommodative intraocular lens ("IOL") devices have the risk of becoming nonoperational or providing poor visual quality in the case of a power or system failure. Embodiments of the present disclosure comprise accommodating IOL devices configured to correct for far- and/or near-sighted vision and to provide good image quality and extended depth of field ("EDOF") capabilities even in cases of system failure. In some embodiments, the accommodative IOL devices described herein provide good visual quality by maintaining monofocal vision quality and providing extended depth of field even in an unpowered situation. The accommodative IOL devices described herein are configured to provide clear corrective vision and high image quality to patients having various visual deficits and various pupil sizes.

In some embodiments, the accommodating IOL devices described herein include an electro-active optical component and a passive optical component that are separable and distinct parts of the device. Such embodiments may facilitate implantation through a smaller incision than a conventional monolithic electro-active accommodative implant. In some instances, the accommodating IOL devices described herein can be implanted in the eye to replace a diseased lens (e.g., an opacified natural lens of a cataract patient). In other instances, the accommodating IOL devices described herein may be implanted in the eye sulcus 32 (shown in FIG. 1) anterior to the natural lens. In some embodiments, the accommodating IOL devices described herein include multiple optical components that may be configured to complement each other and to cooperate to enhance the patient's vision while being implanted in different regions of the eye. In some embodiments, the accommodating IOL devices described herein include an electro-active component positioned within an opaque ring that functions to reduce unwanted optical aberrations caused by the edges of the electro-active component. In some embodiments, the embodiments described herein comprise features described in U.S. Nonprovisional application Ser. Nos. 15/175,106, filed Jun. 7, 2016 and 15/159,079, filed May 19, 2016.

FIG. 1 is a diagram of an eye 10 showing some of the anatomical structures related to the surgical removal of cataracts and the implantation of IOLs. The eye 10 comprises an opacified lens 12, an optically clear cornea 14, and an iris 16. A lens capsule or capsular bag 18, located behind the iris 16 of the eye 10, contains the opacified lens 12, which is seated between an anterior capsule segment or anterior capsule 20 and a posterior capsular segment or posterior capsule 22. The anterior capsule 20 and the posterior capsule 22 meet at an equatorial region 23 of the lens capsule 18. The eye 10 also comprises an anterior chamber 24 located in front of the iris 16 and a posterior chamber 26 located between the iris 16 and the lens capsule 18.

A common technique of cataract surgery is extracapsular cataract extraction ("ECCE"), which involves the creation of an incision near the outer edge of the cornea 14 and an opening in the anterior capsule 20 (i.e., an anterior capsulotomy) through which the opacified lens 12 is removed. The lens 12 can be removed by various known methods including phacoemulsification, in which ultrasonic energy is applied to the lens to break it into small pieces that are promptly aspirated from the lens capsule 18. Thus, with the exception of the portion of the anterior capsule 20 that is removed in order to gain access to the lens 12, the lens capsule 18 remains substantially intact throughout an ECCE. The intact posterior capsule 22 provides a support for the IOL and acts as a barrier to the vitreous humor within the vitreous chamber. Following removal of the opacified lens 12, an IOL may be implanted within the lens capsule 18, through the opening in the anterior capsule 20, to restore the transparency and refractive function of a healthy lens. The IOL may be acted on by the zonular forces exerted by a ciliary body 28 and attached zonules 30 surrounding the periphery of the lens capsule 18. The ciliary body 28 and the zonules 30 anchor the lens capsule 18 in place and facilitate accommodation, the process by which the eye 10 changes optical power to maintain a clear focus on an image as its distance varies.

Figure 2:
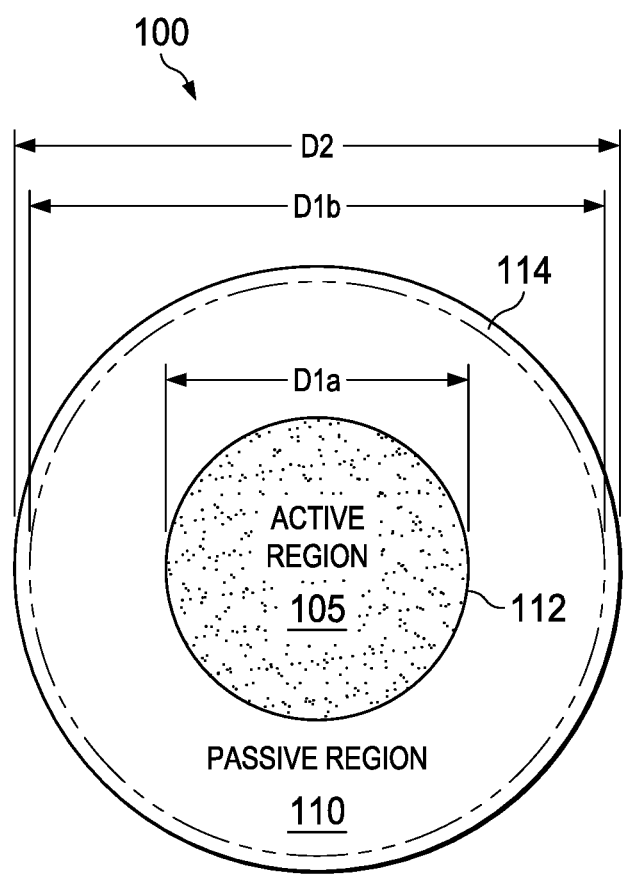
FIG. 2 illustrates a front view of an exemplary accommodative IOL device according to one embodiment consistent with the principles of the present disclosure.
Figure 3A:
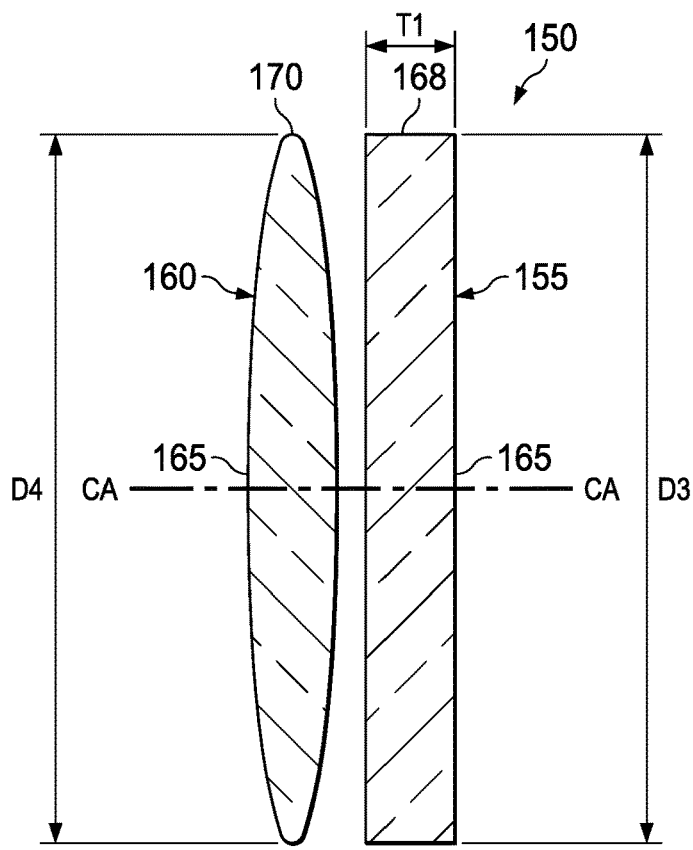
FIG. 3A illustrates a cross-sectional view of an exemplary accommodative IOL device according to another embodiment consistent with the principles of the present disclosure.

FIG. 2 illustrates a front view of an exemplary accommodative IOL device 100 according to one embodiment consistent with the principles of the present disclosure. The accommodating IOL devices described herein are configured to provide clear vision and accommodation capability using an electro-active or active component in addition to a passive component. In exemplary embodiments disclosed herein, the accommodative IOL device 100 comprises a circular and at least partially flexible disc configured to be implanted in the lens capsule 18 or the eye sulcus 32. As shown in FIGS. 2 and 3, the accommodative IOL device 100 is shaped as a generally circular disc comprising an active region 105 and a passive region 110. In some embodiments, the active region 105 and the passive region 110 comprise a single lens. In other embodiments, for example as shown in FIGS. 3A and 4A, the active region 105 and the passive region 110 form separate optical components that may be shaped and configured to couple together.

In the pictured embodiment, the active region 105 occupies a central region of the IOL device 100, while the passive region 110 extends to a peripheral region of the IOL device 100. The active region 105 is shaped and configured as a generally circular component. In other embodiments, the active region 105 may have any of a variety of shapes, including for example rectangular, ovoid, oblong, and square. In some embodiments, the active region 105 includes a refractive index that is different than the refractive index of the passive region 110.

The electro-active or active region 105 may comprise any of a variety of materials having optical properties that may be altered by electrical control. The active region 105 comprises an electro-active element that can provide variable optical power via any available tunable optics technology including, by way of non-limiting example, moving lenses, liquid crystals, and/or electro-wetting. Although the alterable properties described herein typically include refractive index and optical power, embodiments of the invention may include materials having other alterable properties, such as for example, prismatic power, tinting, and opacity. The properties of the materials may be affected and controlled electrically, physically (e.g., through motion), and/or optically (e.g., through light changes). The active region 105 has an adjustable optical power based on electrical input signals controlling the region, so that the power of the accommodative IOL device 100 can be adjusted based on the patient's sensed or inputted accommodation demand. The accommodative IOL device 100 may include control circuitry, power supplies, and wireless communication capabilities. In some embodiments, this componentry may be packaged in a biocompatible material and/or sealed electronic packaging.

Figure 4:
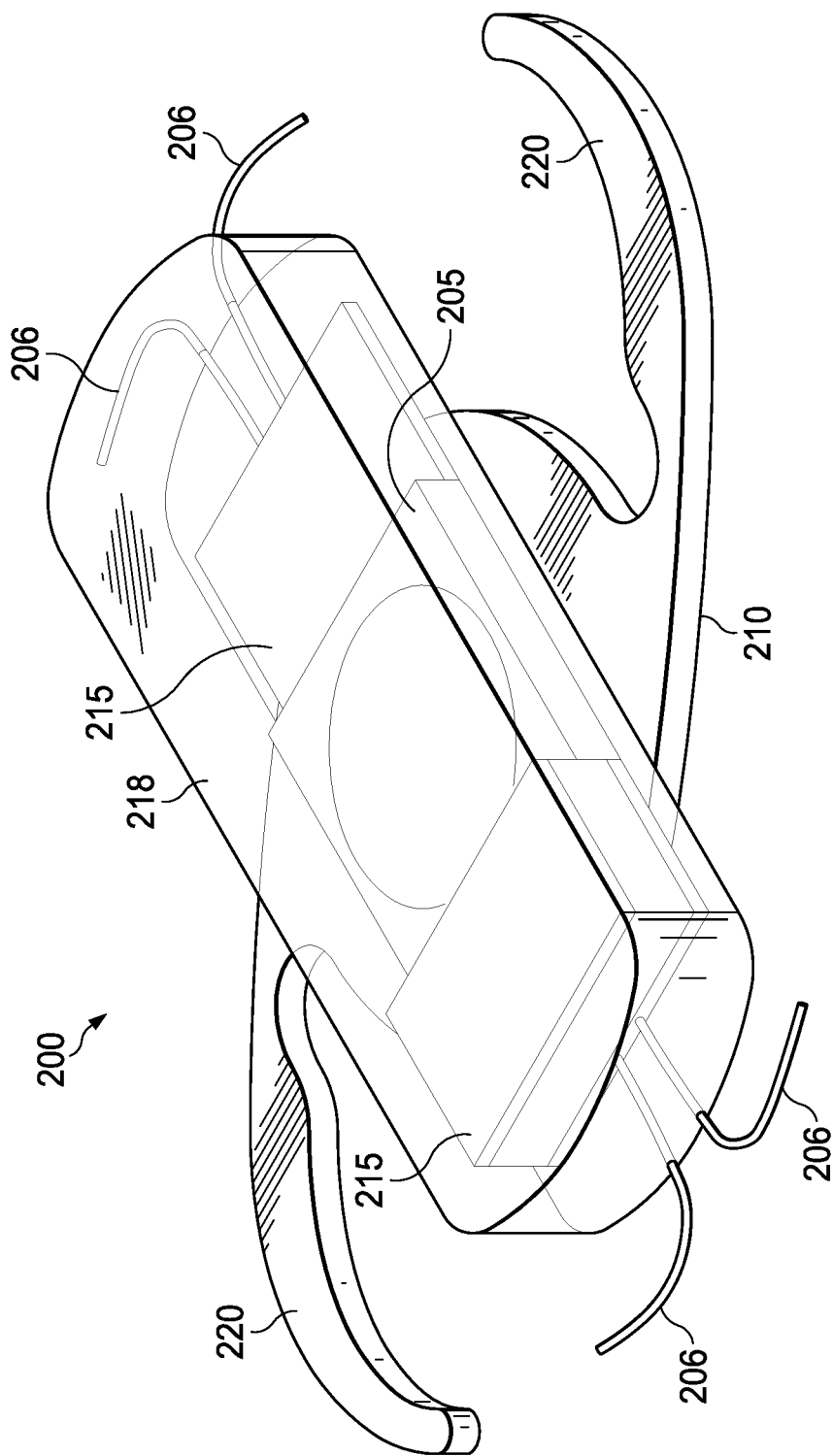
FIG. 4 illustrates a perspective view of an exemplary accommodative IOL device according to an embodiment of the present disclosure.

In some embodiments, the passive region 110 is shaped and configured as an annular ring encircling the active region 105. In other embodiments, the passive region 110 is shaped and configured as a separate disc adjacent to the active region 105, as shown in FIG. 3A. The passive region 110 may include a refractive index that is different than the refractive index of the active region 105. The passive region 110 and the active region 105 are formed from any of a variety of biocompatible materials. In general, the passive region 110 is formed of relatively more flexible materials than the active region 105. In some embodiments, the active region 105 may be associated with several other components designed to power and control the active region, as shown in FIG. 4. Although the outer diameter D1a of the active region 105 is shown as substantially smaller than an outer diameter D2 of the passive region 110 in the pictured embodiment, the outer diameter D1a of the active region 105 may be sized larger relative to an outer diameter D2 of the passive region 110 in other embodiments. In the pictured embodiment, the active region 105 includes a diameter D1a that is smaller than a diameter D2 of the passive region 110. However, in other embodiments, as indicated by the dotted line, an outer diameter D1b of the active region 105 may be almost as large (or equivalent to) as the outer diameter D2 of the passive region 110. In various embodiments, the outer diameter D1 of the active region 105 may range from 3 mm to 6 mm, and the outer diameter D2 of the passive region 110 may range from 6 mm to 12 mm. For example, in one exemplary embodiment, the outer diameter D1 of the active region 105 may be 3 mm, and the outer diameter D2 of the passive region 110 may be 6 mm.

The accommodative IOL device 100 is designed and optimized to have matching focuses (or matching focal points) for both the active region 105 and the passive region 110 to provide a focused image on the retina 11 for far objects for all pupil sizes. As the object draws closer to the eye 10, the optical power of the active region 105 may be adjusted in response to the input signal (e.g., the electrical input signal) to keep the image focused on the retina 11. This provides accommodation to the patient in a similar manner as a healthy natural crystalline lens.

In some embodiments, the active region 105 may be associated with several other components designed to power and control the active region, as shown in FIG. 4. If the active region 105 cannot be powered due to, by way of non-limiting example, a system failure or an empty battery, the active region 105 is shaped and configured to act, in conjunction with the passive region 110, like a passive or monofocal lens. In an exemplary embodiment, the unpowered active region 105 has the same optical power as the passive region 110. However, the active region 105 may perform as a passive lens having a different optical power than the passive region 110 because of thickness and refractive index differences between the two regions.

FIG. 3A illustrates a cross-sectional view of an exemplary accommodative IOL device 150 according to another embodiment consistent with the principles of the present disclosure. The accommodating IOL device 150 is configured to provide clear vision and accommodation capability using an electro-active or active component in addition to a passive component. The accommodative IOL device 150, like the accommodative IOL device 100 described above, may be used to replace the opacified natural lens 12 of cataract patients and provide the patient with clear vision and enhanced accommodative ability.

Figure 3B:
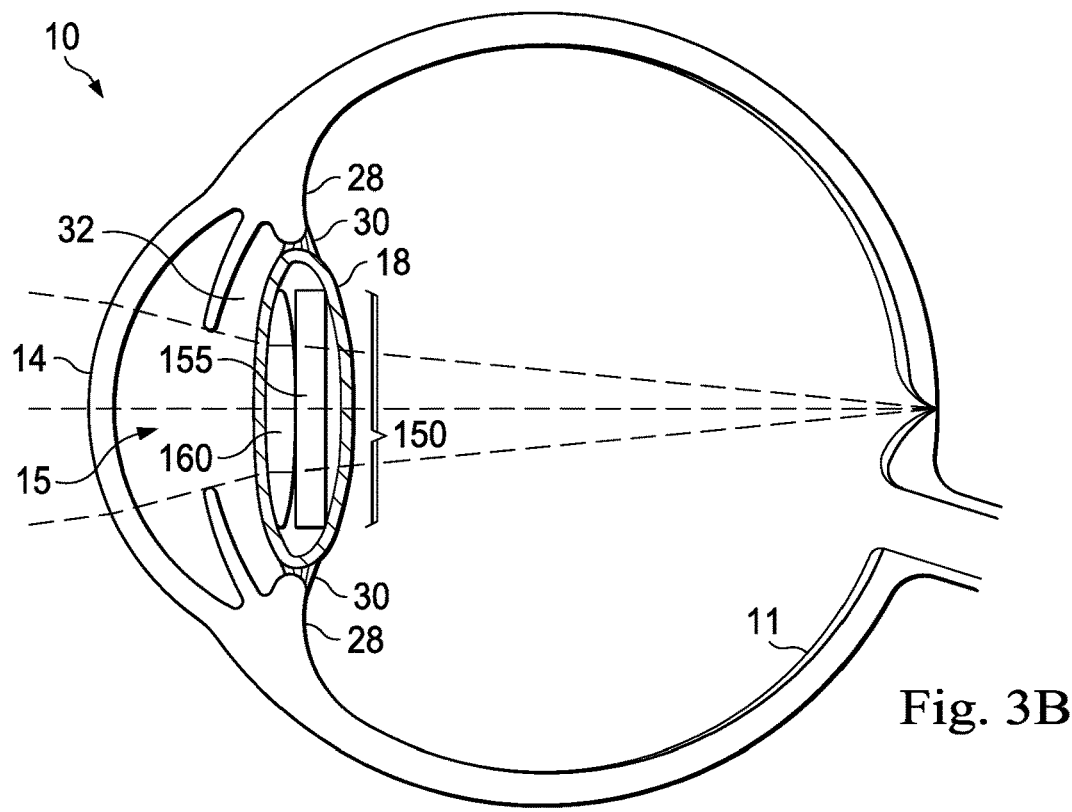
FIG. 3B illustrates a cross-sectional view of the exemplary accommodative IOL device shown in FIG. 3A positioned within the eye in a manner consistent with the principles of the present disclosure.

As shown in FIGS. 3A and 3B, the accommodative IOL device 150 comprises an electro-active or active element 155 and a passive element 160. Except for the differences described below, the active element 155 may have substantially similar properties to the active region 105 described above with reference to FIGS. 2 and 3. Except for the differences described below, the passive element 160 may have substantially similar properties to the passive region 110 described above with reference to FIGS. 2 and 3. Unlike in the accommodative IOL device 100, where the active region 105 and the passive region 110 are part of a single, monolithic optical component, the active element 155 and the passive element 160 of the accommodative IOL device 150 comprise two individual and separable optical components.

Figure 7:
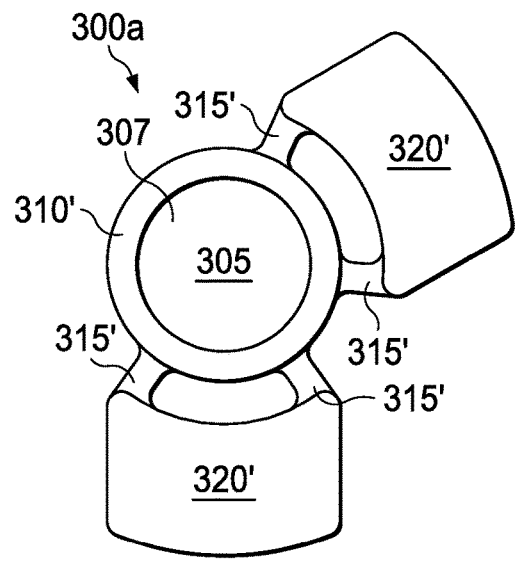
FIGS. 7-14 illustrate front views of different exemplary accommodative IOL devices according to various embodiments consistent with the principles of the present disclosure.

As shown in FIGS. 3A and 3B, the active element 155 and the passive element 160 form separate optical components or regions that are shaped and configured to function together. In the pictured embodiment, both the active element 155 and the passive element 160 are shaped and configured as generally circular optical components that allow for the passage of light beams through the accommodative IOL device 150 toward the retina 11. In other embodiments, the active element 155 may have any of a variety of shapes, including for example rectangular, ovoid, oblong, and square. In some embodiments, the active element 155 may be associated with several other components designed to power and control the active element, as shown in FIG. 7. The active element 155 includes a thickness T1 that may range from 0.2 mm to 2 mm. For example, in one exemplary embodiment, the thickness T1 of the active element 155 may be 0.6 mm. In some embodiments, the thickness T1 of the active element 155 varies from the center of the active region 155 to a periphery 168 of the active region 155. For example, in some embodiments, the active element 155 may taper in thickness from its center to its periphery 168. Although an outer diameter D3 of the active element 155 is shown as substantially similar to an outer diameter D4 of the passive element 160 in the pictured embodiment, the outer diameter D3 of the active element 155 may be larger or smaller than an outer diameter D4 of the passive element 160 in other embodiments. In particular, the optical performance of embodiments having more flexible active elements 155 may benefit from having active elements 155 that are sized to be larger than the passive elements 160.

A peripheral edge 170 comprises the outermost circumferential region of the passive element 160. In some instances, as shown in FIG. 3A, the peripheral edge 170 comprises the outermost circumferential edge of the accommodative IOL device 150. In some embodiments, the accommodative IOL device 150 may taper toward the peripheral edge 170 to facilitate stabilization of the accommodative IOL device 100 inside the lens capsule 18 and/or the eye sulcus 32. This may allow the accommodative IOL device 150 to be self-stabilized and self-retained in the eye 10 (i.e., without the use of sutures, tacks, or a manually held instrument). In some embodiments, the angle of the taper from the passive element 160 towards the peripheral edge 170 is selected to substantially match the angle of the equatorial region 23 in the lens capsule 18, thereby facilitating self-stabilization of the accommodative IOL device 150 within the eye 10.

FIG. 3B illustrates a cross-sectional view of the exemplary accommodative IOL device 150 shown in FIG. 3A positioned within the eye in a manner consistent with the principles of the present disclosure. In the pictured embodiment, the accommodative IOL device 150 comprises an at least partially flexible device configured to be implanted in the lens capsule 18 or the eye sulcus 32 (i.e., the area between the iris 16 and the lens capsule 18). In general, the passive element 160 is relatively more flexible than the active element 155. In one embodiment, the passive element 160 is a large diameter, foldable, relatively soft lens, while the active element 155 is a relatively rigid device having a smaller diameter than the passive element 160.

In the pictured embodiment shown in FIGS. 3A and 3B, the active element 155 is positioned posterior to the passive element 160 within the lens capsule 18 of the eye 10. In other embodiments, the accommodative IOL device 150 may be positioned within the eye such that the active element 155 is positioned anterior to the passive element 160 within the eye 10 (i.e., closer to the anterior chamber 24 of the eye 10). In both instances, the active element 155 and the passive element 160 are positioned to be aligned along a central axis CA extending perpendicularly through a central region 165 of the device 150. In some instances, the active element 155 and the passive element 160 may be positioned within separate regions of the eye 10.

The active component 155 and the passive component 160 do not necessarily need to be implanted into the eye 10 at the same time. The active component 155 and the passive component 160 may be implanted within the eye 10 sequentially during the same ophthalmic procedure, or may be implanted into the eye 10 in separate procedures, which may occur at different times. In some instances, the active element 155 may be implanted into an eye 10 that already contains a passive lens (i.e., a non-accommodating IOL), thereby offering the possibility of presbyopia correction to a pseudophakic patient.

In some embodiments, in its expanded condition, the accommodative IOL device 150 comprises a substantially circular device configured to be self-stabilized within the eye 10 (e.g., within the lens capsule 18 or the sulcus 32). In some embodiments, the accommodative IOL device 150 comprises a substantially circular device having haptic supports 220, as described below in relation to FIG. 4, configured to be self-stabilized within the eye 10 (e.g., within the lens capsule 18 or the sulcus 32).

The passive element 160 and/or the active element 155 may be shaped and configured to maintain the natural circular contour of the lens capsule 18 and to stabilize the lens capsule 18 in the presence of compromised zonular integrity when the accommodative IOL device 150 is positioned in the eye 10. In some embodiments, the passive element 160 comprises a generally circular disc with a substantially circular shape configured to match the substantially circular cross-sectional shape of the lens capsule 18 when the lens capsule 18 is divided on a coronal plane through an equatorial region 23. In some embodiments, the device 150 (i.e., the active element 155 and/or the passive element 160) may taper from the central region 165 of the device 150 towards a peripheral edge 170. The peripheral edge 170 comprises the outermost circumferential region of the accommodative IOL device 150. In some embodiments, the accommodative IOL device 150 may taper toward its peripheral edge 170 to facilitate stabilization of the accommodative IOL device 100 inside the lens capsule 18 and/or the eye sulcus 32. This may allow the accommodative IOL device 150 to be self-stabilized and self-retained in the eye 10 (i.e., without the use of sutures, tacks, or a manually held instrument). In some embodiments, the angle of the taper from the central region 165 towards the peripheral edge 170 is selected to substantially match the angle of the equatorial region 23 in the lens capsule 18, thereby facilitating self-stabilization of the accommodative IOL device 150 within the eye 10.

Figure 5:
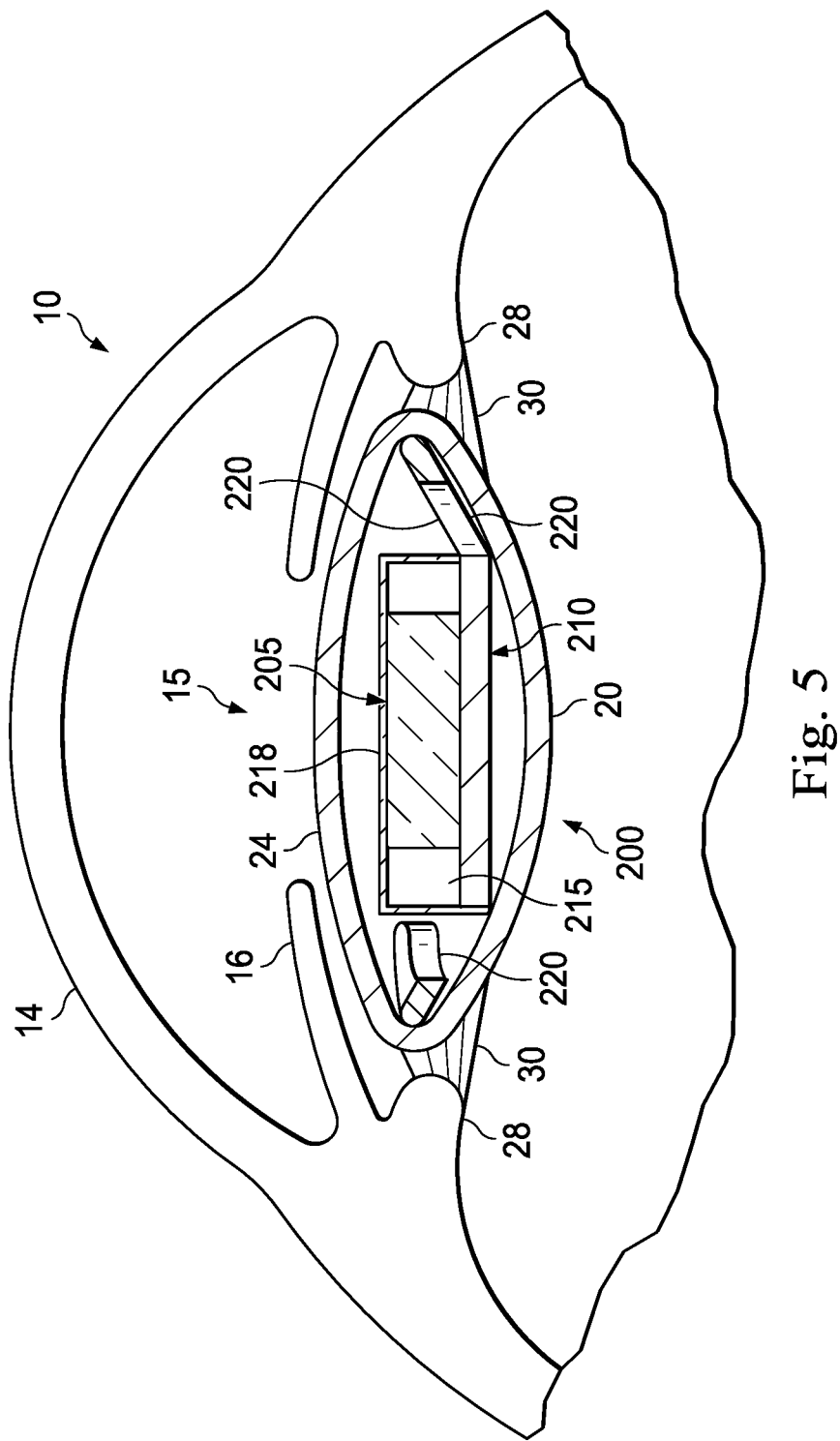
FIG. 5 illustrates a cross-sectional view of the exemplary accommodative IOL device shown in FIG. 4 implanted within the eye according to one embodiment of the present disclosure.

FIG. 4 illustrates a perspective view of an exemplary accommodative IOL device 200 according to one embodiment of the present disclosure. FIG. 5 illustrates a cross-sectional view of the exemplary accommodative IOL device 200 shown in FIG. 4 implanted within the eye 10 according to one embodiment of the present disclosure.

The exemplary accommodative IOL device 200 shown in FIGS. 4 and 5 is substantially the same as the accommodative IOL device 150 shown in FIGS. 3A and 3B except for the differences mentioned below. Similar to the accommodative IOL device 150, the accommodative IOL device 200 comprises a two-element IOL including an active component 205 and a passive component 210. The active component 205 is substantially the same as the active element 155 described above. In the pictured embodiment shown in FIG. 4, the accommodative IOL device 200 comprises additional components 215 (e.g., power sources, circuitry, control modules, antennae, etc.) related to the operation of the electro-active element 155. Several of the additional components 215 and the active element 205 are shown gathered together within a housing 218. The passive component 210 is substantially the same as the passive component 160 described above except for the differences described herein.

In some instances, the two-element accommodative IOL device 200 (and the IOL device 150) can offer enhanced stability of the device and improved protection for the structures of the eye 10 in comparison to conventional IOL devices. For example, in some embodiments, as shown in FIGS. 4 and 5, the passive element 210 may act as an anchoring structure for the active element 205. Moreover, if positioned behind or posterior to the active element 205, the softer passive element 210 can act as a cushion during the implantation procedure of the active element 205 as well as during other procedures such as laser posterior capsulotomies.

In the pictured embodiment, the accommodative IOL device 200 comprises a substantially circular device including haptic supports 220, as shown in FIG. 4, configured to be self-stabilized within the lens capsule 18 of the eye 10 (or the sulcus 32), as shown in FIG. 5. The haptic supports 220 comprise substantially pliable, curved, elongate members extending outwardly from the accommodative IOL device 200. In the pictured embodiment, the haptic supports 220 extend radially from the passive element 210. In other embodiments, the haptic supports 220 may extend from the active element 205. The haptic supports 220 are shaped and configured to expand into the lens capsule 18 and/or the sulcus 32 to stabilize and anchor the IOL device 200 within the eye 10. The haptic supports 220 may be shaped and configured to maintain the natural circular contour of the lens capsule 18 and to stabilize the lens capsule 18 in the presence of compromised zonular integrity when the accommodative IOL device 200 is positioned in the eye 10. In the pictured embodiment, the IOL device 200 includes centralizing members 206 that are shaped and configured to stabilize and centralize the IOL device 200 within the lens capsule 18 of the eye 10 (or the sulcus 32). Other embodiments lack centralizing members 206.

Figure 6A:
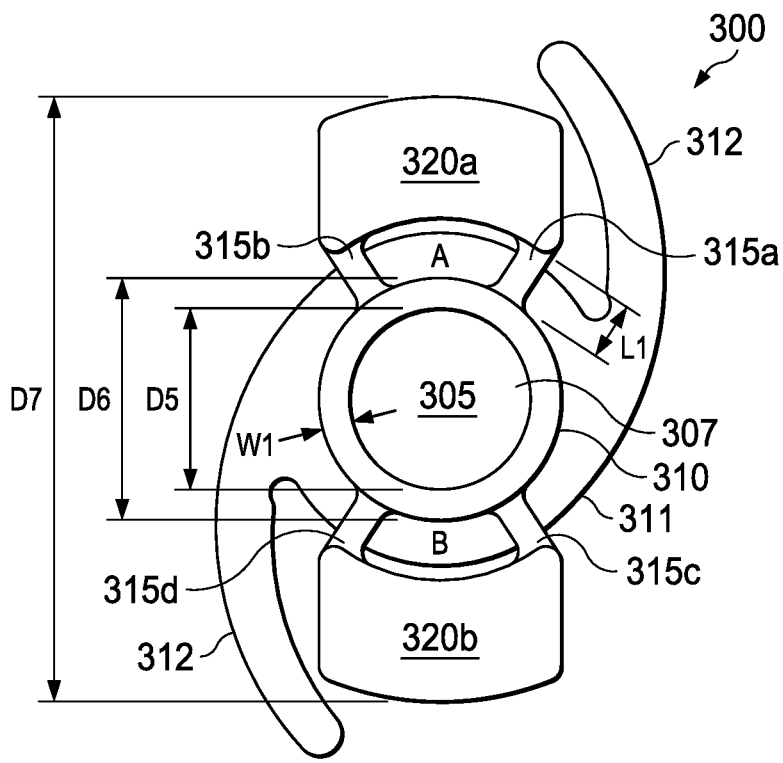
FIGS. 6A and 6B illustrate an exemplary accommodative IOL device according to another embodiment consistent with the principles of the present disclosure.
Figure 6B:
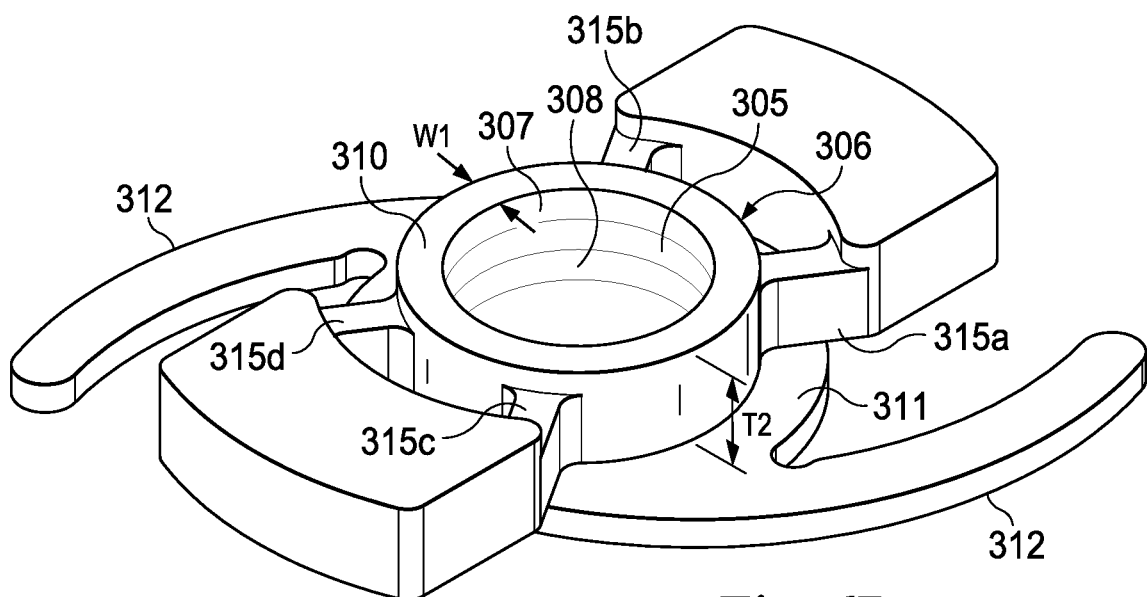

FIGS. 6A and 6B illustrate an exemplary accommodative IOL system 300 according to another embodiment consistent with the principles of the present disclosure. The system 300 provides high image quality to patients of all pupil sizes and object locations, as well as acceptable distance vision in the case of power failure. In some instances, the system 300 may be used to replace the opacified natural lens of cataract patients and can provide clear vision and accommodation capability to these patients. The accommodative IOL system 300 comprises an optical element 305 positioned within a housing 306. In the pictured embodiments, the optical element 305 is hermetically sealed within the housing 306. The housing 306 comprises a transparent anterior window 307, a transparent posterior window 308, and an opaque frame 310. In the pictured embodiments, the optical element 305 is sandwiched between the transparent anterior window 307 and the transparent posterior window 308, and is circumferentially surrounded by the opaque frame 310. The opaque frame 310 may be continuous with the transparent windows 307, 308. In the pictured embodiment, the system 300 includes four support legs 315a, 315b, 315c, and 315d that extend between the opaque frame 310 and two peripheral housings 320a, 320b.

The optical element 305 may comprise either solely an active component or a two-element accommodative lens having both active and passive components. For example, in some embodiments, as shown in FIGS. 6A and 6B, the optical element 305 may be substantially identical to the active element 155 described above in relation to FIG. 3A. In such embodiments, the accommodative IOL system 300 may include a passive element or a passive component positioned outside the housing 306, as shown in FIG. 6B. The embodiment shown in FIG. 6B features a passive component 311 including haptic supports 312, which are substantially similar to the passive component 210 and the haptic supports 220, respectively, described above in relation to FIG. 4. In FIGS. 7-14, although the passive component 311 is not shown, it is understood that the accommodative IOL systems 300a-300h may include the passive component 311 as shown in FIGS. 6A and 6B.

In other embodiments, the optical element 305 may comprise a two-element accommodative lens substantially identical to the accommodative IOL device 100 described above in relation to FIG. 2. If the passive element 160 is sized smaller than or equivalent to the active element 155, both the active element 155 and the passive element 160 may be contained within the housing 306. These embodiments may appear substantially similar to the embodiments pictured in FIGS. 7-14 (with the passive element 160 positioned within the housing 106 either anterior or posterior to the active element 155). Thus, the optical element 305 may provide variable optical power via any available tunable optics technology, including, without limitation, moving lenses, liquid crystals, and electro-wetting. In some instances, the optical element 305 provides variable optical power to mainly correct for presbyopia.

In one instance, after implantation within the eye 10, the optical element 305 may be held in place centrally in the eye optical path by the housing 306. The opaque frame 310 can reduce the unwanted optical effects caused by the phase transitions and stray light caused by the edges of the optical element 305 (and, in particular, by the edges of the active element 155 of the optical element 305). The opaque frame 310 can reduce the optical aberrations in the area outside the optical element 305.

The opaque frame 310 and the transparent anterior and posterior windows 307, 308 completely enclose the optical element 305. The anterior and posterior windows 307, 308 are transparent to allow for the passage of light through the optical element 305. The opaque frame 310 comprises an opaque ring that is shaped and sized to securely encircle or frame the periphery of the optical element 305. In the pictured embodiment, the opaque frame 310 is shaped as a ring or annulus that is sized and shaped to mimic the circular shape of the optical element 305. In other embodiments, the opaque frame 310 may be any shape that snugly surrounds the circumferential periphery of the optical element 305. Thus, the opaque frame 310 may echo the shape or peripheral outline of the optical element 305. The opaque frame 310 can be formed of any of a variety biocompatible materials, including, without limitation, titanium, ceramics, sapphire, quartz, and glass. The opaque frame 310 includes an inner diameter D5 that measures slightly larger than the outer diameter of the optical element (e.g., in some instances, the outer diameter D3 of the active element shown in FIG. 3A). In one embodiment, the inner diameter D5 measures 3 mm. In one embodiment, the outer diameter D6 measures 3.4 mm. In one embodiment, the width W1 measures 0.2 mm. . In one embodiment, the thickness T2 (shown in FIG. 6B) measures 1.4 mm. The size of the opaque frame 310 may vary in different embodiments.

In the pictured embodiment, as mentioned above, the system 300 includes four support legs 315a, 315b, 315c, and 315d that extend between the opaque frame 310 and two peripheral housings 320a, 320b. The support legs 315a-d comprise relatively thin supports for the opaque frame 310 extending radially outward from the opaque frame to the peripheral housings 320a, 320b. The support legs 315a-d comprises hollow, tubular structures extending between the opaque frame 310 and the peripheral housings 320a, 320b. In some instances, the support legs 315a-d are formed of the same material as the opaque frame 310. In other instances, the support legs 315a-d are formed of a different biocompatible material than the opaque frame 310. In some embodiments, the support legs 315a-d may be opaque. In other embodiments, the support legs 315a-d may be optically clear. The area that is marked by the letter A represents empty space between the peripheral housing 320a, 320b, the legs 315a and 315b, and the opaque frame 310. The area that is marked by the letter B represents empty space between the peripheral housing 320a, 320b, the legs 315c and 315d, and the opaque frame 310. The peripheral housings 320a, 320b have an arcuate shape and are held in an orbital position by the legs. The system 300 includes an outer diameter D7 that is sized to fit within the lens capsule 18. In some instances, the outer diameter D7 is approximately 10 mm. In other instances, the outer diameter D7 ranges from 8 mm-13 mm.

In some embodiments, the exemplary accommodative IOL system 300 includes a power source and controlling electronics contained within the peripheral housings 320a, 320b. The support legs 315a-d can house the electrical connectors and contacts linking the active component of the optical element 310 with such peripheral electronics. The optical element 305 and the opaque frame 310 may be connected to the power source and the controlling electronics by electrical connections and contacts housed within the support legs 315a-d. The support leg 315a has a length L1 that may range from 0.5 mm to 5 mm. In one embodiment, the length L1 measures 1 mm. In the pictured embodiment, each of the support legs 315a-d have the same length L1. In other embodiments, each individual support leg 315a-d may have a different length.

In the pictured embodiments, the support legs 315a-d are substantially linear and straight. In other embodiments, one or more of the support legs 315a-d may be curved or bent along its length. The size, profile, number, thickness, and arrangement of the support legs may vary between different embodiments, as shown in FIGS. 11-14.

FIGS. 11-14 illustrate different exemplary accommodative IOL systems 300a-300h including an optical element 305 according to various embodiments consistent with the principles of the present disclosure. The structure of the accommodative IOL systems 300a-h, including the shape and size of the opaque frame 310, the shape, size, and number of peripheral housings 320, and the shape, size, and number of support legs 315, may vary. In each of the following embodiments shown in FIGS. 11-14, although the accommodative IOL systems 300a-h differ structurally from the system 300 shown in FIG. 6, the opaque frame, the housings, and the support legs in the systems 300a-h are substantially similar to the opaque frame 310, the peripheral housings 320, and the support legs 315a-d in purpose and function. For the sake of simplicity, the opaque frames, support legs, and peripheral housings in FIGS. 11-14 are uniformly identified by the indicators 310', 315', and 320', respectively.

Figure 9:
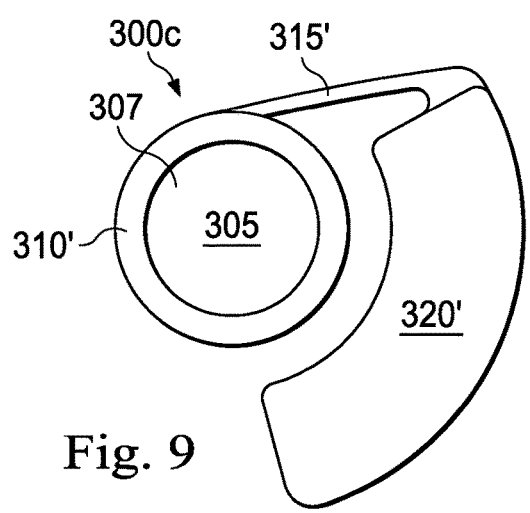

The number, size, and arrangement of the support legs 315' and the peripheral housings 320' may be selected in consideration of, among other factors, the type of condition to be treated, the patient's particular anatomy, or the type of optical element 305 to be placed within the opaque frame 310'. The spaces between the opaque frames 310', the support legs 315', and the housings' lower the overall volume of the accommodative IOL systems 300a-h and preserve a healthcare practitioner's ability to perform fundus exams. In some embodiments, these spaces increase the flexibility, contractibility, and expandability of the accommodative IOL devices 300a-h. In most embodiments, the arrangement of the opaque frames 310', the support legs 315', and the peripheral housings 320' allow the free circulation of aqueous humor within the lens capsule, which may inhibit lens epithelial cell proliferation. In the pictured embodiments shown in FIGS. 11-12 and 14-18, the peripheral housings 320' are arranged symmetrically about the opaque frame 310'. In other embodiments, as shown in FIG. 9, the peripheral housing 320' and the leg 315' may be arranged asymmetrically about the opaque frame 310'. The embodiments may include an even or an odd number of peripheral housings 320'.

FIG. 7 illustrates an exemplary accommodative IOL 300a including two peripheral housings 320' attached to the opaque frame 310' by four support legs 315'. Instead of being disposed opposite one another (i.e., approximately 180° apart) as in the embodiment shown in FIG. 6, the two peripheral housings 320' are positioned closer to one another along the circumference of the opaque frame 310'. For example the peripheral housings 320' may be positioned approximately 135° apart.

Figure 8:
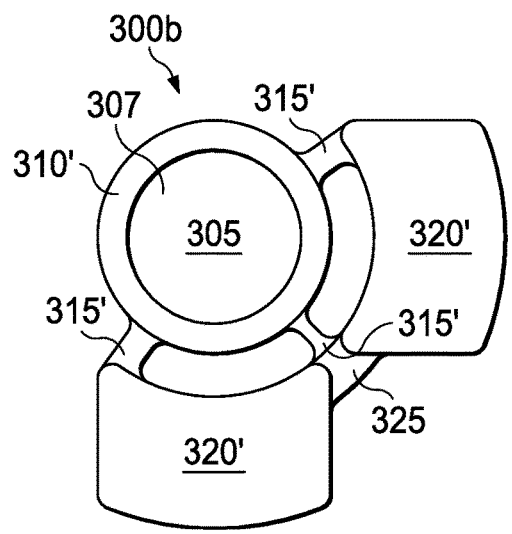

FIG. 8 illustrates an exemplary accommodative IOL 300b including two peripheral housings 320' attached to the opaque frame 310' by three support legs 315'. Instead of being disposed opposite one another as in the embodiment shown in FIG. 6, the two peripheral housings 320' are positioned at approximately right angles to one another in relation to the opaque frame 310'. In the pictured embodiment, the central support legs 315' is shaped to be less thick than the other two support legs 315'. In various embodiments, the support legs 315' may be shaped and sized uniformly or differently from one another. In the pictured embodiment, the two peripheral housings 320' are also connected to one another by a bridge support 325. Electrical connectors and/or other active IOL components may extend between the peripheral housings 320' through the bridge support 325.

FIG. 9 illustrates an exemplary accommodative IOL 300c including one peripheral housing 320' attached to the opaque frame 310' by a single slender support leg 315'. The support leg 315' extends tangentially from the frame 310' to an outer edge of the peripheral housing 320'. In the pictured embodiment, the peripheral housing 320' is sized to be larger, with a greater arc of curvature, than the peripheral housings 320 shown in FIG. 6. The arc of curvature is sized to provide enough volume within the peripheral housing to contain any desired electronics and power supply. For example, in some embodiments, the arc of curvature measures approximately 60 degrees. Other arcs of curvature are contemplated. Using a slender support leg 315' can allow for a more open optical path beyond the optical element 305. This could prove advantageous in low-light conditions as it permits more light to reach the retina, which may allow for better visualization of the retina during fundus exams/procedures.

Figure 10:
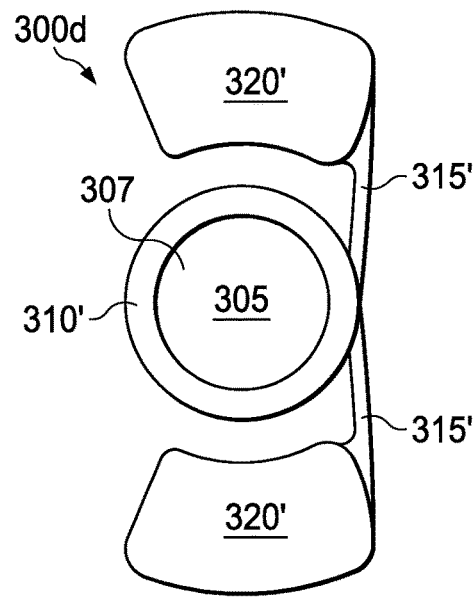

FIG. 10 illustrates an exemplary accommodative IOL 300d including two peripheral housings 320' attached to an opaque frame 310' by two support legs 315'. The support legs 315' extend tangentially from the perimeter of the optical element 305', with each leg 315' coupled to an outer edge of a respective peripheral housing 320'. In the pictured embodiment, the two support legs 315' are more slender than the support legs 315 shown in FIG. 6, and the support legs 315' are both disposed on the same side of the opaque frame 310'. In some instances, relatively thinner support legs 315*a-d* can provide increased flexibility, which may facilitate implantation within the eye 10.

Figure 11:
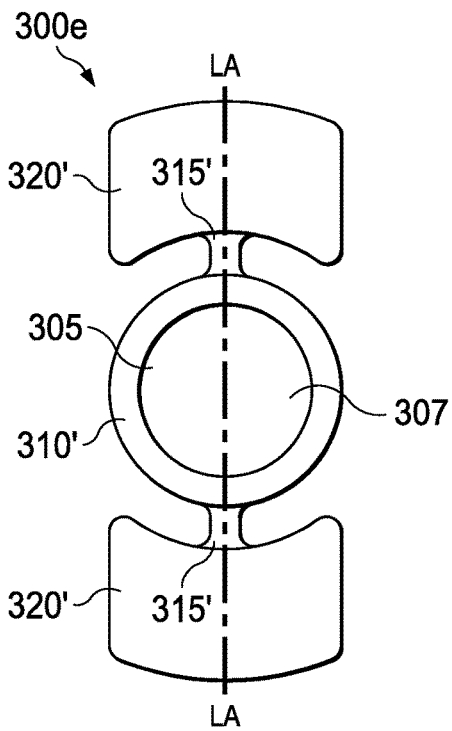

FIG. 11 illustrates an exemplary accommodative IOL 300*e* including two peripheral housings 320' attached to an opaque frame 310' by two support legs 315'. In the pictured embodiment, each of the two support legs 315' extend from the midline of the opaque frame 310' and connect to a central region of each of the peripheral housings 320'. Each of the two support legs 315' extend along a common linear axis LA extending through the center of the optical element 305.

Figure 12:
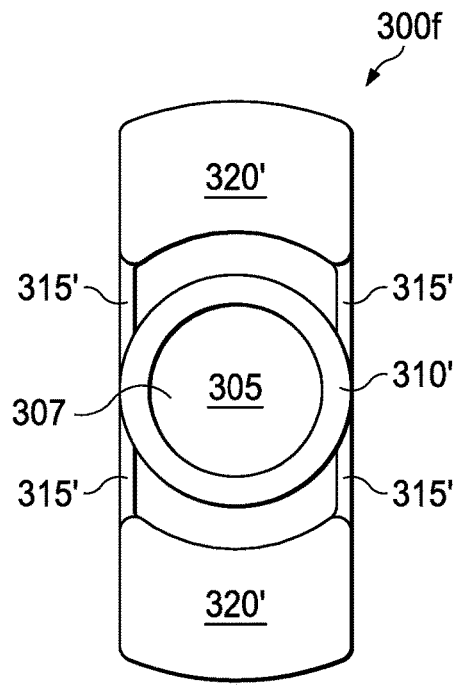

FIG. 12 illustrates an exemplary accommodative IOL 300*f* including two peripheral housings 320' attached to the opaque frame 310' by four slender support legs 315'. The support legs 315' attach tangentially to the peripheral circumference of the opaque frame 310' and extend to the outer edges of the respective peripheral housings 320'.

Figure 13:
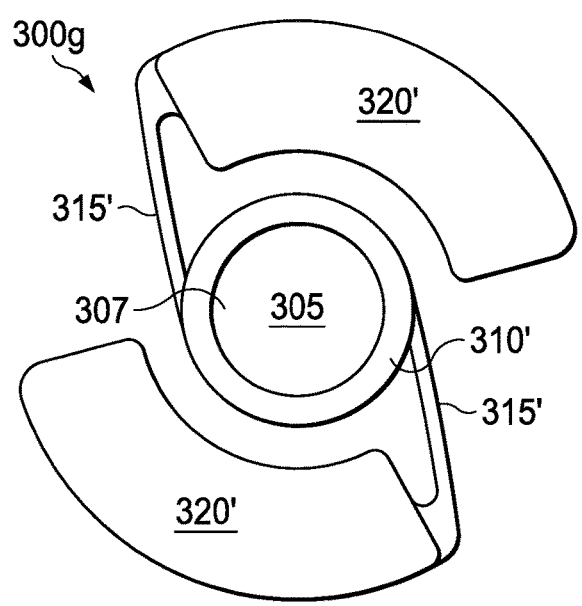

FIG. 13 illustrates an exemplary accommodative IOL 300*g* including two peripheral housings 320' attached to the opaque frame 310' by two slender, curved support legs 315'.

Figure 14:
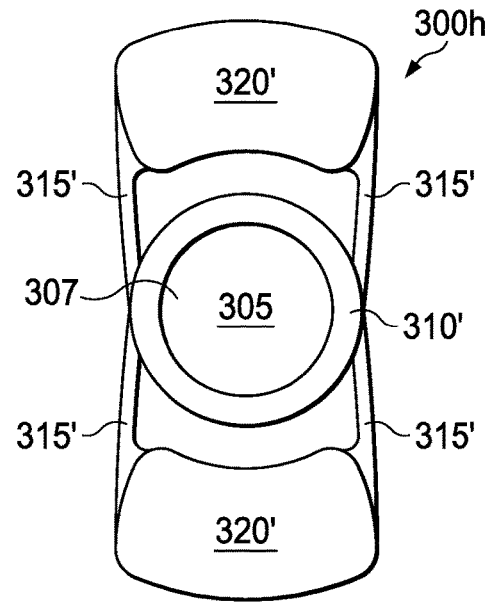

FIG. 14 illustrates an exemplary accommodative IOL 300*h* including two peripheral housings 320' attached to the opaque frame 310' by four slender, curved support legs 315'. In the pictured embodiment, each of the four support legs 315' extend from the peripheral circumference of the opaque frame 310' to connect to the lateral sides of the peripheral housings 320'.

The accommodative IOL devices and systems described hererin may be formed from any of a variety of biocompatible materials having the necessary optical properties to perform adequate vision correction as well as requisite properties of resilience, flexibility, expandability, and suitability for use in intraocular procedures. In some embodiments, the individual components of the accommodative IOL devices described herein may be formed of different biocompatible materials of varying degrees of pliancy. For example, in some embodiments, the passive region 110 and the passive elements 160 and 210 may be formed of a more flexible and pliant material than the active region 105 and the active elements 155 and 205 to minimize contact damage or trauma to intraocular structures. In other embodiments, the reverse relationship may exist. The accommodative IOL devices described herein may be coated with any of a variety of biocompatible materials, including, by way of non-limiting example, polytetrafluoroethylene (PTFE).

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An implantable accommodative IOL system for insertion into an eye of a patient, the system comprising:
    an optical element comprising an active optical element having variable optical power, wherein:
        the active optical element is configured to receive an electrical input signal; and
        the active optical element comprises a material with optical properties that are adjustable based on the electrical input signal;
    a housing comprising a transparent anterior window, a transparent posterior window, and an opaque frame circumferentially disposed around a periphery of the optical element, wherein the active optical element is sealed within the housing between the transparent anterior window and the transparent posterior window such that the active optical element is configured to remain within the sealed housing between an anterior side and a posterior side of the opaque frame throughout an entire range of variable optical power; and
    a passive optical element disposed outside of the sealed housing, wherein the passive optical element is aligned with the active optical element.

2. The accommodative IOL system of claim 1, wherein the opaque frame circumferentially encircles the transparent anterior window and the transparent posterior window.

3. The accommodative IOL system of claim 1, further comprising electronic components coupled to the optical element.

4. The accommodative IOL system of claim 3, wherein the electronic components include a power source.

5. The accommodative IOL system of claim 1, wherein the active optical element has a first thickness and first refractive index.

6. The accommodative IOL system of claim 5, wherein:
    the passive optical element has a second thickness and second refractive index, and
    a light beam passing through the active element has a phase difference from the light beam passing through the passive element.

7. The accommodative IOL system of claim 6, wherein the second refractive index is different than the first refractive index.

8. The accommodative IOL system of claim 6, wherein the second thickness is different than the first thickness.

9. The accommodative IOL system of claim 1, wherein the opaque frame is shaped and configured to contour the peripheral outline of the optical element.

10. The accommodative IOL system of claim 3, further comprising a peripheral housing shaped and configured to contain the electrical components coupled to the optical element.

11. The accommodative IOL system of claim 10, further comprising at least one support leg coupled to the passive optical element and configured to house electrical connections extending between the electrical components in the peripheral housing and the optical element.

12. The accommodative IOL system of claim 11, wherein the at least one support leg comprises a hollow, tubular structure extending between the peripheral housing and the opaque frame.

13. The accommodative IOL system of claim 11, wherein the at least one support leg is shaped as a linear support extending between the opaque frame and the peripheral housing.

14. The accommodative IOL system of claim 11, wherein the at least one support leg is shaped as a curved support extending between the opaque frame and the peripheral housing.

15. The accommodative IOL system of claim 11, wherein the at least one support leg is optically clear.

16. The accommodative IOL system of claim 11, wherein at least one of the opaque frame, the at least one peripheral housing, and the at least one support leg comprises a flexible, self-expanding biocompatible material.

17. An implantable accommodative IOL system, comprising:
   an active optical element having variable optical power and comprising a material with optical properties that are adjustable based on an electrical input signal;
   a housing comprising a transparent anterior window, a transparent posterior window, and an opaque frame circumferentially disposed around a periphery of the active optical element, wherein the active optical element is sealed within the housing between the transparent anterior window and the transparent posterior window;
   a passive optical element disposed outside of the sealed housing, wherein the passive optical element is aligned with the active optical element;
   a peripheral housing configured to contain electronic components in electrical communication with the active optical element; and
   a plurality of support legs coupling the peripheral housing to the active optical element, wherein:
   each of the plurality of support legs provides a sealed channel configured for housing electrical connections between the electronic components and the active optical element, and
   each of the plurality of support legs has a length sufficient to position the peripheral housing at a distance from the opaque frame such that there is an empty space between the passive optical element, the peripheral housing, and the plurality of support legs.

18. The implantable accommodative IOL system of claim 17, wherein at least one of the plurality of support legs is shaped as a curved support extending between the opaque frame and the peripheral housing.

19. The implantable accommodative IOL system of claim 17, wherein at least one of the plurality of support legs is optically clear.

20. The implantable accommodative IOL system of claim 17, wherein the opaque frame circumferentially encircles the transparent anterior window and the transparent posterior window.

* * * * *